US006478938B1

(12) United States Patent
Paek et al.

(10) Patent No.: US 6,478,938 B1
(45) Date of Patent: Nov. 12, 2002

(54) ELECTROCHEMICAL MEMBRANE STRIP BIOSENSOR

(75) Inventors: Se-Hwan Paek, Taejeon (KR); Joung-Hwan Cho, Incheon (KR)

(73) Assignee: Bio Digit Laboratories Corporation, Seoul (KR)

( * ) Notice: Subject to any disclaimer, the term of this patent is extended or adjusted under 35 U.S.C. 154(b) by 92 days.

(21) Appl. No.: 09/593,663

(22) Filed: Jun. 14, 2000

(30) Foreign Application Priority Data

May 24, 2000 (KR) ........................................ 2000-27949

(51) Int. Cl.$^7$ ............................................. G01N 27/327
(52) U.S. Cl. ........................ 204/403.01; 204/403.03; 204/403.06; 422/70; 422/82.02
(58) Field of Search ............................. 204/403, 403.01, 204/403.03, 403.06; 422/70, 82.02; 436/514, 518, 525

(56) References Cited

U.S. PATENT DOCUMENTS

| | | | | |
|---|---|---|---|---|
| 5,858,666 A | * | 1/1999 | Weiss | 204/400 |
| 6,319,670 B1 | * | 11/2001 | Sigal et al. | 435/6 |
| 6,331,244 B1 | * | 12/2001 | Lewis et al. | 204/403 |
| 6,333,200 B1 | * | 12/2001 | Kaler et al. | 204/194 |

FOREIGN PATENT DOCUMENTS

JP 2000-65835 * 3/2000

OTHER PUBLICATIONS auto–translation from the Japanes Patent Office website of JP 2000–65835.*
R. M. Albrecht et al., Immunocytochemistry: A Practical Approach, 1993, pp. 151–176, Oxford University Press, Oxford.
J .H. Peterman, Immunochemistry of Solid–Phase Immunoassay, 1991, pp. 47–65, CRC Press, London.
C. P. Price et al., Principles and Practice of Immunoassay, 1997, pp. 581–603, Macmillan Reference Ltd. London.
J. Roth, Techniques in Immunocytochemistry, vol. 2, 1983, pp. 217–284, Academic Press, London.
M. M. Bradford, 1976, Anal. Biochem. vol. 72, pp. 248–254.
G. Cavelier, 1995, Bioelectroch Bioener, vol. 40, pp. 197–213.
J. H. Cheung et al., 1997, Macromolecules, vol. 30, pp. 2712–2716.
R. T. da Rocha et al., 1997, J. Chem. Edu., vol. 74, pp. 572–574.
A. de Diego et al., 1997, Electrochem. Acta, vol. 42, pp. 1449–1456.

(List continued on next page.)

Primary Examiner—Robert J. Warden, Sr.
Assistant Examiner—Kaj K. Olsen
(74) Attorney, Agent, or Firm—Finnegan, Henderson, Farabow, Garrett & Dunner LLP

(57) ABSTRACT

The present invention is directed to the development of a biosensor based on the immuno-chromatographic method that can provide an assay speed and convenience required for point-of-care (the doctor's office and emergency room) testing or home-version diagnosis. Though certain physical symptoms, such as pregnancy and ovulation, or bacterial infection may be identified by a qualitative analysis for the presence of indicating substances, most analytes for clinical investigation demand their concentrations known in specimens. Therefore, the inventors of the present invention have developed a novel biosensor by combining the immuno-chromatographic method and the electric conductivity detection technology so that on-site quantitative determination at the points of care or at home may be carried out.

13 Claims, 6 Drawing Sheets

OTHER PUBLICATIONS

A. Heller, 1990, Acc. Chem. Res. vol. 23, pp. 128–134.
M. P. A. Laitinen, 1996, Viosens. Bioelectron., vol. 11, pp. 1207–1214.
S. H. Paek et al., 1999, Anal. Lett. vol. 32, pp. 335–360.
O. Quadrat et al., 1998, Synthetic Met, vol. 97, pp. 37–42.
T. A. Sergeyeva et al., 1998, Biosens. Bioelectron., vol. 13, pp. 359–369.
J. Stejskal et al., 1996, Polymer, vol. 37, pp. 367–369.
T. M. Swager, 1998, Acc. Chem. Res., vol. 31, pp. 201–207.
X.-L. Wei et al., 1996, JACS, vol. 118, pp. 2545–2555.
X. Wei et al., 1995 Synth. Met. vol. 74, pp. 123–125.
J.-H. Kim et al., Feb. 2000, Biosensors & Bioelectronics vol. 14, pp. 907–915.

* cited by examiner

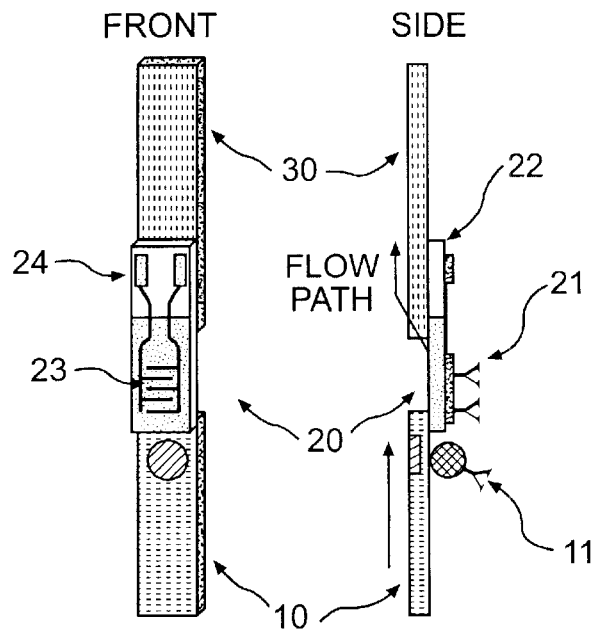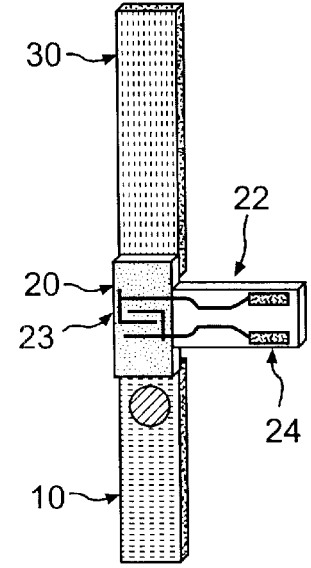
Fig. 2aa     Fig. 2ab
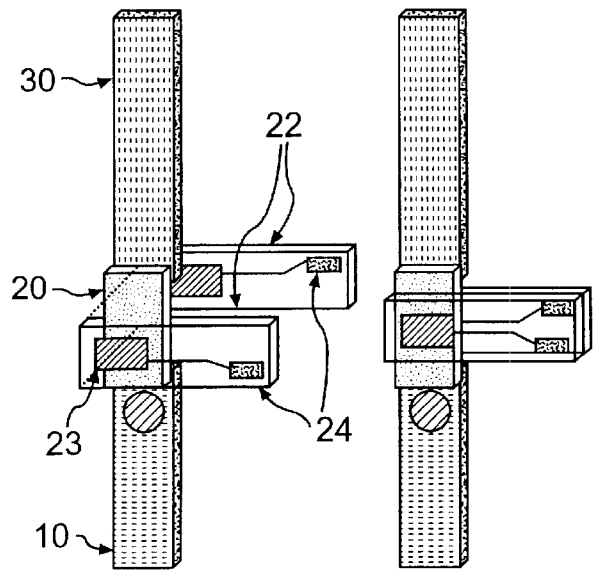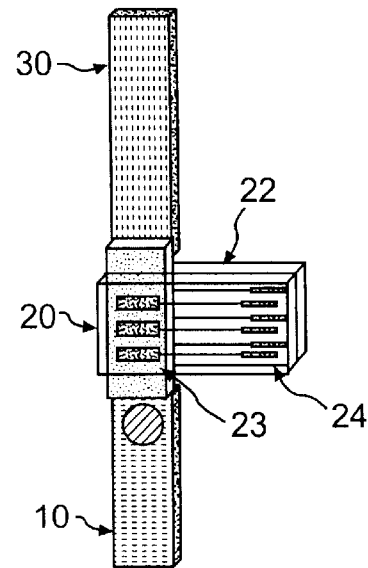
Fig. 2b     Fig. 2c

ELECTROCHEMICAL MEMBRANE STRIP BIOSENSOR

FIELD OF THE INVENTION

The present invention relates to a novel assay to provide a quick and accurate quantitative determination of analytes such as hormones, proteins and enzymes while utilizing the principle of immunochromatographic method.

PRIOR ARTS

Indicator substances such as hormones, proteins and microorganisms that enable expectation and progression of human diseases have relatively complex structure, and thus they are mostly determined by immunoassays using antigen-antibody reaction. Such examinations have been generally carried out in specialized laboratories. However, the need of on-site examination at the point-of-care such as hospitals or emergency rooms and even at home, is growing rapidly (Reference: C. P. Price et al., Principles and Practice of Immunoassay, 1997, page 579–603, Macmillan Reference Ltd., London). To this end, immunoassay system which does not require any expert knowledge and complex procedure, and is simple to use and provides quick responses, has been developed, and such diagnostic performance could be somewhat achieved by an immuno-chromatography method, which employs microporous membrane for immobilizing a binding protein (e.g. antibody) (Reference: M. P. A. Laitinen, 1996, Biosens. Bioelectron. Vol. 11, 1207–1214; S. H. Paek et al., 1999, Anal. Lett., Vol. 32, 335–360). When the analyte-containing sample is absorbed from the bottom end of the membrane strip, the analyte is transported to the layer of immobilized binding protein by the capillary action through membrane pores. A binding reaction between the analyte and the binding protein occurs on the surface of solids, and unbound molecules are subsequently separated by the medium flow. As the transfer of reactants is accelerated by the lateral flow of medium, the above membrane immuno-chromatography method provides a quick analysis of analyte and convenience of one-step detection where the analysis is completed upon sample application alone.

An immuno-strip model system to perform immuno-chromatographic assay comprises the following three membrane strips ((a) of FIG. 1). From the bottom, glass fiber membrane (10) for sample application, nitrocellulose (NC) membrane (20) with immobilized binding protein (21) specific to analyte, and cellulose membrane (30) as absorbent are shown. These membrane strips are partially superimposed and arranged on a plastic film and fixed by double-sided tape. Considering the analytical procedure, a conjugate (11) between binding protein and signal generating substance (e.g. gold colloid particles, enzymes, colored plastic beads) is added on a predetermined site of the glass fiber membrane, and a medium (2) containing the analyte (1) is absorbed from the bottom end of immuno-strip. The analyte is transported to the upper part of the strip by the medium flow that is induced by the capillary action, and binds to the conjugate through immune reaction upon contact with binding protein in the conjugate ((b) of FIG. 1). When the medium carries the binding complex to the binding protein immobilized on the NC membrane, the binding complex is captured by the immobilized binding protein through immune reaction (the site on the antigen molecule recognized by this binding protein is different from the recognized by the binding protein conjugated with signal generator ((c) of FIG. 1). Uncaptured components are transferred by the medium flow for separation to the absorbent cellulose membrane. Such sandwich-type complex formed on a defined site on the membrane (complex where two binding protein molecules are bound to both sides of the analyte molecule at the same time) generates a color signal (25) detectable by the naked eye because it includes the indicator, color generating substance.

Such a qualitative analytical mode of the system may be sufficient for the identification of certain physical symptoms or infections causing diseases, but most substances for clinical investigation demand analyte concentration known in each specimen. If quantitation is desired, the color signal can be converted to optical density by adopting a photometric transducing capability, yet because of difficulty in reproducible conversion and poor detection sensitivity, it is not widely used.

Therefore, it has been required to develop a novel quantitative method to determine analyte concentration more simply and accurately relative to photometry, while directly using the immuno-chromatographic method that is simple to use and provides a quick response.

SUMMARY OF THE INVENTION

The present inventors have completed the present invention based on the idea that gold colloids used as signal generating substance in the above immuno-chromatography method are metal particles with conductivity.

Thus, the object of the present invention is to provide a more convenient, accurate and novel quantitative analysis. In other words, the object of the present invention is to provide a novel quantitative as well as qualitative method of electrochemical assay with convenience and sensitivity for various analytes such as hormones, proteins and enzymes, while using the principle of immuno-chromatography.

BRIEF DESCRIPTION OF THE DRAWINGS

FIG. 2 shows electrochemical membrane strip biosensors of the present invention having various screen-printed thick-film electrodes.

DETAILED DESCRIPTION OF THE INVENTION

The present invention relates to an electrochemical membrane strip biosensor comprising a first membrane pad for sample application, a second membrane pad for signal generation where a binding protein specific to analyte is immobilized and at least one pair of electrodes are screen-printed, a third membrane pad as absorbent and a conjugate between metal colloids as signal generating substance and a binding protein.

Figure 1:
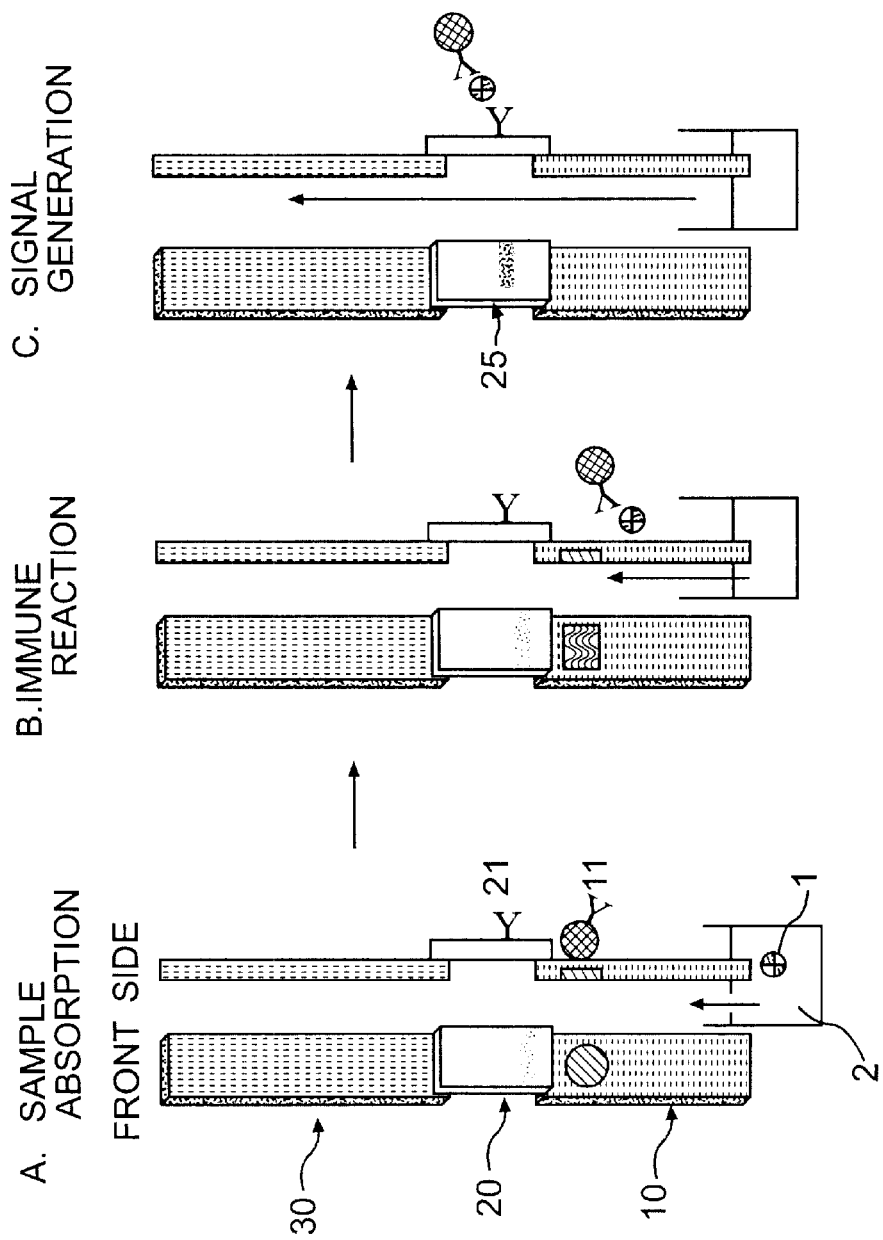
FIG. 1 shows a conventional membrane strip immuno assay system based on immuno-chromatographic method and the concept of qualitative detection using thereof.

The membrane pads for sample application (10), signal generation (20) and absorption (30), and the conjugate are identical with those used for the conventional immunochromatography method (see (a) of FIG. 1) except that the electrodes are screen-printed on the signal generation membrane.

As material for the pads, any material can be used as long as it is suitable for the purpose of each pad. As a typical example, glass fiber membrane can be used as sample application membrane pad, nitrocellulose membrane as signal generation membrane pad, and cellulose membrane as absorption membrane pad.

The binding protein is a component that reacts specifically with the analyte, and for an example, marker antibody, enzyme or receptor can be included. Therefore, the biosensor according to the present invention can be applied to the manufacture of enzyme sensor and gene sensor using enzymatic reaction and nucleic acid hybridization, respectively, as well as immune reaction system based on antigen-antibody reaction.

The binding protein immobilized on the signal generation membrane pad and that in the conjugate specifically react with the identical analyte, but the binding sites on the analyte are different from each other.

As for the metal colloids, gold colloids, silver colloids and iron colloids can be used, preferably gold colloids.

In the electrochemical membrane strip biosensor of the present invention, the conjugate may be added in a dried state in advance to the sample application membrane pad, or stored in a separate container and added just prior to the analysis.

In the electrochemical membrane strip biosensor according to the present invention, the conjugate, i.e. metal colloids, distributes on the signal generation membrane surface by the reaction of the analyte in the binding complex, between the analyte and the conjugate, with the binding protein immobilized on the surface, and the density of the metal colloids is converted to a conduction signal across the two electrodes screen-printed on the signal generation pad. The conduction signal is in proportion to the density of the metal particle (i.e. analyte concentration).

In the electrochemical membrane strip biosensor of the present invention, the electrodes may be screen-printed on the signal generation membrane pad according to the conventional screen-printing techniques. For example, an electrode material paste (platinum, gold, silver and carbon etc.) may be printed directly on the membrane or on an insulator through a patterned screen and baked at an elevated temperature (generally 100° C.) and the same procedure is repeated. At this time, the binding protein immobilized on the signal generation membrane pad is positioned between a pair of electrodes. In case of printing the electrodes on an insulator, the insulator may be located at one or both side(s) of the membrane with the immobilized binding protein, and then attached to the membrane by an adequate pressure or tape.

For the electrochemical membrane strip biosensor according to the present invention, any electrode pattern may be used, yet an interdigitated structure is preferred to two-fingered configuration. This is because the surface area between the two electrodes can be greatly increased to raise sensitivity. The signal generation membrane pad can be completed by immobilizing the binding protein on the sensor sites of the membrane where the electrodes are screen-printed.

The electrode patterns that can be applied to the electrochemical membrane strip biosensor of the present invention are as follows.

FIG. 2aa shows an example. An electrode (23) is screen-printed on the signal generation membrane pad (20), and electric contacts (24), i.e., electric connection part to a conductivity meter, are formed on the insulator (22) (e.g. plastic film) which is insulated from an aqueous medium transferred by the absorption to membrane, and positioned on the top of the electrode in the same direction with the signal generation membrane pad (20). The electric contacts (24) can be electrically connected to the screen-printed electrodes by a manual mode.

FIG. 2ab is another example. To increase flexibility in spatial arrangement between the prepared electrochemical membrane strip biosensor and the conductivity meter, the electric contacts (24) are positioned at the lateral side (e.g. in an erect position) of the signal generation membrane pad (20), i.e. biosensor.

Another example is shown in FIG. 2b. In the screen-printed electrodes FIGS. 2aa and 2ab, the sensor part is formed outside of the membrane, and the analyte-binding protein reaction takes place mostly on the inner surfaces of the membrane pores, and thus only a part of the reacted complex contributes to electric conduction. To solve this problem, a pair of electrodes, cathode and anode, are separated from each other by positioning at each side of the membrane, forming a sandwich type. Such method for preparing a sandwich type electrode can be explained as follows:

As for the first method, electrodes can be fabricated by printing each electrode on an insulator such as plastic film and then drying at an elevated temperature, and such prepared pair of electrodes is positioned at the respective side of the membrane, forming a sandwich type. Herein, incomplete contacts between the membrane and electrodes may cause a resistance increase and result in a failure in measuring conductivity. Thus, it is preferable to design a system to give an adequate pressure to the two compartments or to attach the printed electrodes to membrane by using a tape.

As another method, electrodes can be positioned as a sandwich type by directly printing on the both sides of the membrane. In this case, short circuit might occur due to the partial contact between the electrodes.

Another example is shown in FIG. 2c. A number of the sandwich type electrodes in FIG. 2b are simultaneously positioned. In order to construct an assay system for multiple analytes, a number of sensors need to be arranged in a small space. In case of interdigitated structure where a pair of electrodes is arranged at a single plane, as substantial distance should be maintained between the electrodes to prevent short circuit, quite a little area for each sensor is usually required. Therefore, in case of installing multiple interdigitated sensors in one system, since the length of the signal generation membrane pad increases, a change might be caused in the reaction between the analyte and the immobilized binding protein according to the position of the sensor in length. On the other hand, in case of sandwich type electrode as in FIG. 2c, the distance between a pair of electrodes is determined by the membrane thickness, thus adjacent electrodes can be arranged with a minimum distance apart in an erect position on a single plane. Therefore, in case of using sandwich type electrodes, a multi-sensor can be established in a small spaced signal generation membrane pad while minimizing variation against analyte-binding protein reaction. In addition to the electrode patterns as explained above, other electrodes varied in shape and arrangement can be constructed.

Other reagents unbound to the binding protein of the signal generation membrane pad are transferred by the flow of medium and absorbed to the absorption pad. Therefore, as for the absorption pad, anyone can be utilized, if suitable for such purpose.

As metal colloids generating quantitative signal in the electrochemical membrane strip biosensor of the present invention are metal, electric conduction takes place along the metal colloid particles bound on the signal generation membrane pad, and the signal increases in proportion to the arranged metal particle density (i.e., eventually, analyte concentration). Therefore, the electrochemical membrane strip biosensor of the present invention provides far superior advantages in comparison to the conventional immunochromatographic assay based on photometry. First, the binding reaction participating in the circuit may elevate conduction in an exponential degree because the accumulation repetitively shortens the mean distance between the gold colloids bound on the surfaces (Reference: A. Heller, 1990, *Acc. Chem. Res.*, Vol. 23, 128–134). Therefore, such formed electric signal is amplified comparing to the conventional color signal just based on photometry (Reference: T. M. Swager, 1998, *Chem. Res.*, Vol. 31, 201–207). Secondly, the conduction can be measured using an ordinary conductivity meter that is readily available in most laboratories. The device used is stable, accurate, relatively cheap, and simple to operate (Reference: R. T. da Rocha et al., 1997. *J. Chem. Edu.*, Vol. 74, 572–574). Finally, since the gold tracer is visible, the assay progress can be followed by the naked eye and the colored signal can be preserved for subsequent reference after carrying out the quantitative determination.

In the chromatographic assay, when preparing the binding protein-metal conjugate, i.e., the signal generator, the particles are surrounded with protein molecules such as immunoglobulin and casein as blocking agent for reducing non-specific interaction, that render an ionic polymer shell on the outside of the gold. This may interfere with electron hopping, a dominant process of charge transfer between conducting mediators (Reference: G. Cavelier, 1995, Bioelectroch. Bioener. Vol. 40, page 197–213; A. Heller, 1990, *Acc. Chem. Res.*, Vol. 23, 128–134). Because protein molecules could behave similar to amorphous semiconductor, the molecule layer thickness exceeding the distance (2 to 2.5 nm) required for efficient electron relay acts as a barrier against conduction. To reduce such resistance, blocking can be carried out using polyethylene glycol that is open and relatively extended outside of the metal particle surface. Under the given conditions, the signal-to-noise ratio is enhanced as compared with that from the ionic protein coating. However, a resistance to conduction in the polymer layer still exists on the metal surface. Thus, development of a special method to overcome such problem is required.

Figure 3:
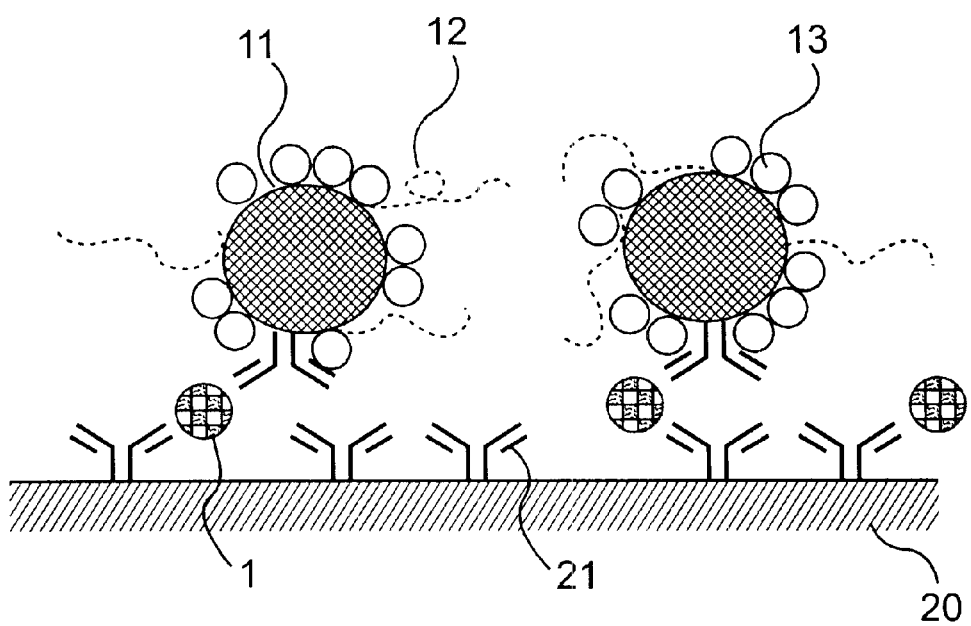
FIG. 3 shows a concept for enhanced electron transfer with a conducting polymer adsorbed on the surface of metal colloids.

Therefore, the electrochemical membrane strip biosensor in the present invention can be utilized with a blocking agent (13), protein, adsorbed on the metallic colloid surfaces and, further, a conducting polymer (12) bound before the adsorption of the blocking protein onto the metal particle surfaces (see FIG. 3). As blocking protein that can be used in the present invention, bovine serum albumin, casein, gelatin etc. can be enumerated as described above, and as conducting polymer, polyaniline, polypyrrole, polythiophene and poly (p-phenylene). Among the conducting polymers given above, polyaniline is the most preferably in the present invention. The polymeric conductor molecules existing on the particle surfaces may bridge the neighboring metal particles or being them closer to improve the change-transfer state. The conducting polymer is an organic functional substance on which intensive studies have been pursued with respect to such applications as energy conservation, color changeable element, electrochemical detector, electromagnetic screening material, capacitor, ion gate etc., since they are highly conductive and exhibit a large electron transfer rate via oxidation/reduction.

As another conductivity modulating method, a doping method can be adopted, where carbocation or carboanion is introduced by a chemical treatment of electron carrier or receptor existing in an energy gap of the polymer chain.

Although the conducting polymer exhibits a high conductivity, it is poorly soluble in an aqueous solution, which may diminish its functionality as molecular wire in the present invention. Therefore, the following methods can be used to improve such property of the polymer.

1) Method of doping by using an ionic salt. As examples of ionic salt, LiCl, $LiClO_4$ and $LiBF_4$ can be listed.

2) Method of chemical binding of redox molecules onto the conducting polymer together with the application of the method 1). Ferrocene and ruthenium can be enumerated as examples of the redox substance.

3) Method of adding a counterion against the conducting polymer. For example, a sulfonated polystyrene can be used as counterion to polyaniline.

Therefore, it is preferable to prepare the metal colloids-binding protein conjugate, which generates a conductimetric signal upon capture, in the presence of analyte (1), by another binding protein (21) immobilized on the signal generation membrane pad (20), according to the following method (see FIG. 3). After conjugating the binding protein onto the metal colloid particle surface (11) by chemical reaction or physical adsorption, the selected conducting polymer (12) can be subsequently adsorbed. When the conducting polymer is added to the metal particle-binding protein conjugate, the molecules diffuse over the metal surface and are adsorbed onto the residual sites to form an arranged polymer layer (Reference: J. H. Cheung et al., 1997, *Macromolecules*, Vol. 30, 2712–2716). Finally, the residual surfaces of metal particles are blocked with a blocking protein (13) as mentioned above.

When the concentration of conducting polymer is too high, a polymer strand may cause cross-linking between metal particles, resulting in aggregation, thus optimization of the polymer concentration is required against the function as signal generator. In case of polyaniline, a concentration range of 0.01 to 1 mg/ml is preferred.

When carrying out an analysis using the conductimetric biosensor in the present invention, the performance is affected by physical conditions (e.g. temperature; Reference: A. de Diego et al., 1997, *Electrochim. Acta*. Vol. 42, 1449–1456; O. Quadrat. et al., 1998, *Synthetic Met*, Vol. 97, 37–42) as well as chemical conditions (e.g. the concentrations of each ion; Reference: A. de Diego et al., 1997, *Electrochim. Acta*. Vol. 42, 1449–1456; Sergeyeva et al., 1998, *Biosens. Bioelectron*. Vol. 13, 359–369) of the aqueous medium carrying analyte besides the qualities of the respective compartment. While a change of temperature can be simply corrected by a compensation logic installed within the detector, ionic interferences are difficult to estimate and correct because various ions modulate the conductivity in different ways. Therefore, the chemical composition of the medium such as ionic concentrations and pH should be appropriately optimized toward the signal-to-noise ratio.

It is preferable to maintain the acidity of the medium in a neutral pH (pH 5 to 8), and thus a buffer solution can be used. As a buffer solution that can be used as medium, phosphate buffer and Tris buffer can be enumerated. The concentration of a buffer is selected within a minimum range required for dissolving protein in order to suppress the noise. A preferred range is 5 to 50 mM.

However, the neutral acidity provides an optimal condition for antigen-antibody reaction, but may be unsuitable for polyaniline that maintains doped state under acidic conditions (Reference: J. Stejskal et al., 1996, *Polymer*, Vol. 37, 367–369). Therefore, the performance of the precision of conductimetric assay can be improved by performing the antigen-antibody reaction under the neutral condition and then measuring the electric signal under an acidic pH (e.g. pH 2) via pH shift, which provides best conditions for each process, i.e., bio-reaction and signal generation.

On the other hand, analyte-containing specimen may contain ions interfering conductimetric measurement. Such a potential problem can be resolved by adopting the multi-sensor system with two or more signal detection sites (FIG. 2c). The respective signals in proportion to single or multiple analytes are measured by one or more sensors based on analyte-binding protein reactions, and the noise due to the presence of ionic conductivity detected by the remaining sensor and excluded from the detected signal(s), thereby the non-specific interference due to medium can be eliminated.

The principle of the present invention is based on the specific reaction between analyte and the binding protein. As a typical example, antigen-antibody reaction shows a high specificity in view of characteristics of selected antibodies, and also demonstrates a very high binding affinity, providing sensitivity enough to detect analyte present in an extremely low concentration. Further, the present invention provides universality to the measurement of different analytes by merely employing the reaction partners (i.e. specific antibody, enzyme, receptor) in the identical sensor system, and thus can be applied to the detection of analyte, almost unlimitedly, such as food contaminants (e.g. agricultural chemicals, antibiotics, food poisoning bacteria), environmental hormone (e.g. herbicides, insecticides, dioxines), and biochemical substances (e.g. hormones, proteins, cells) used as indicators for medical diagnostics.

The following Examples and Experimental examples are given with the purpose of providing a better understanding of the object, characteristics, advantages and usefulness of the present invention, but never limits the scope of the present invention. Hereinafter, a membrane strip biosensor is herein enumerated that is constructed using human serum albumin as a model analyte, antibodies specific to the human serum albumin as binding proteins, and gold colloid particles as metal colloid articles, which can be used to determine the concentration of human serum albumin in urine for the diagnosis of renal disease.

Materials

Materials used in Examples and Experimental examples are as follows. Human serum albumin (HSA), gold chloride ($HAuCl_4$), glutaraldehyde, casein (sodium salt form, extracted from milk) and CNBr-activated Sepharose 4B were purchased from Sigma (St. Louis, Mo., USA). Goat antiserum to HSA (IgG fraction, 8.3 mg/ml), aniline, ammonium persulfate (APS), LiCl and silver paste were supplied by International Enzyme (Fallbrook, Calif., USA), Fluka (Switzerland), Yakuri Pure Chemicals (Japan), Junsei Chemical (Japan) and Seoul Chemical Research Laboratory (Korea), respectively. Nitrocellulose (NC) membrane (5 m pore size, with polyester backing) was purchased from Millipore (Bedford, Mass., USA), glass fiber membrane (G6 grade) from Fisher Scientific (Springfield, N.J., USA) and cellulose membrane (qualitative #1 and 3MM chromatography grade) from Whatman (Singapore). Gold colloids with a mean particle size of 20 nm were synthesized by the sodium citrate method (Reference; R. M. Albrecht et al., Immunocytochemistry: A Practical Approach, 1993, page 151–176, Oxford University Press, Oxford; J. Roth, Techniques in Immunocytochemistry, Vol. 2, 1983, page 217–284, Academic press, London). Other reagents used were of analytical grade, and all of the solutions were prepared using deionized water with conductivity below 0.1 $\mu S/cm$.

EXAMPLE 1

Purification of Binding Protein (Antibody to Human Serum Albumin)

To purify the antibody specific to human serum albumin (HSA), the chemical coupling of HSA to CNBr-activated Sepharose 4B gels was carried out as recommended by the manufacturer. Such prepared gels were filled in a glass column (11×200 mm, 7 ml bed volume), and washed with acidic and basic buffers in a cyclic manner three times. After equilibrating the column with 10 mM phosphate buffer containing 140 mM NaCl (pH 7.4, PBS) against gel expansion, 3 ml of the antiserum against HSA was applied to the column and the fractionation of specific antibodies was carried out by utilizing a liquid chromatography system (Model 210, Isco, Lincoln, Nebr., USA). After absorption into the gels, unbound proteins were washed with PBS at a rate of 15 ml/h and the bound was then eluted with 0.1 M glycine buffer (pH 3.0). The fractions including specific antibodies were pooled and dialyzed against a series of buffers, i.e. 50 mM acetate buffer (pH 4.0), 10 mM phosphate (pH 6.0) and then PBS. The antibody solution was subsequently concentrated by ultrafiltration (Amicon, Beverly, Mass., USA), quantified by the Bradford method (M. M. Bradford, 1976, *Anal. Biochem.* Vol. 72, page 248–254), and stored at 20° C. after snap freezing.

EXAMPLE 2

Immobilization of Antibody

The antibody against HSA as purified in Example 1 was chemically immobilized on a signal generation membrane pad by the following method. NC membrane strip (5×20 mm) was used as signal generation membrane pad.

The membranes were treated in 10% (v/v) methanol for 30 min and dried in the air. The surfaces were modified by immersing them in 0.5% (v/v) glutaraldehyde solution for 1 h and then thoroughly washed in deionized water. After drying, 2.5 $\mu l$ of antibody (0.5 mg/ml) diluted with 10 mM phosphate buffer was applied on a predetermined site of the membrane and subsequently incubated in a sealed box maintaining 100% humidity at 37° C. for 1 h. Inactivation of the residual functional groups and blocking of the remaining surfaces were carried out in 100 mM Tris buffer, pH 7.6, containing 0.1% (v/v) Tween-20 for 45 min and then dried.

EXAMPLE 3

Preparation of Metal Colloids-binding Protein Conjugate

To label the antibody purified in Example 1 with colorimetric tracer, the purified antibody was conjugated with colloidal gold (Reference: S. H. Paek et al., 1999, *Anal. Lett.*, Vol. 32, 335–360). The antibody solution was dialyzed against 10 mM phosphate (pH 7.4) and diluted to 150 μg/ml with deionized water. The solution (800 μl) was combined with the gold solution (8 ml) adjusted to pH 9.5, and the mixture was reacted for 30 min. The residual surfaces of the gold particles were blocked by adding 1 ml of 0.1 M Tris, pH 7.6, containing 5% casein (5% Casein-Tris) for 30 min. After spinning down, the supernatant was discarded and 0.5% Casein-Tris buffer was added again. The gold particles were re-precipitated by centrifugation and the supernatant was then removed. The final volume was adjusted to 0.4 ml with 0.5% Casein-Tris and the conjugates formed were stored at 4° C. until used.

EXAMPLES 4 to 6

Preparation of Metal Colloids-binding Protein Conjugate with Conducting Polymer

For the preparation of preferred electrochemical signal generator, a conducting polymer, polyaniline, was synthesized by oxidizing aniline monomer in the presence of APS (X.-L.Wei et al., 1996, JACS, Vol. 118, 2545–2555; X. Wei et al., 1995, Synth. Met, Vol. 74, 123–125). Aniline (0.4 M) diluted in 1 M HCl and APS (0.2 mM) were mixed and reacted for 30 min. The polymerized product was filtered, and the filtrate was reduced with 5 ml/g of phenylhydrazine solution, and 20 ml/g of fuming sulfonic acid was added. After the sulfonation at 5° C. for 1 h, sulfonated polyaniline was synthesized. The product was precipitated at 0° C., filtered, dried and dissolved to a desired concentration.

After combining the antibody solution with the gold colloids for conjugation as described in Example 3, polyaniline solutions diluted with 10 mM phosphate buffer (pH 7.4) in different concentrations (0.01, 0.1 and 1 mg/ml) were added into the mixture of gold and antibody, and then reacted for 30 min. The subsequent steps for blocking and conjugate recovery were identical to those in Example 3 except the presence of LiCl (0.001 to 0.1% (w/v); 0.0236–23.6 mM) in the final solution for suspending the gold particles. Thus, metal colloid-binding protein conjugates where the conducting polymers was incorporated in different concentrations of 0.01, 0.1 and 1 mg/ml polyaniline, respectively, were prepared (Examples 4, 5 and 6).

EXAMPLE 7

Fabrication of Thick-film Electrodes with Immobilized Antibody

To design an electrochemical sensor type of bio-strip, thick film electrodes using NC membrane as solid support were prepared as follows.

NC membrane (5×20 mm) with a backing plastic was washed in deionized water three times and then dried in the air. A silver paste was printed on the membrane through a patterned screen of two-electrode system and baked at 100° C. for 3 min. The same procedure was repeated three times to prepare membrane strip electrodes (two-by-three digit pattern in an interdigitated structure, 4×5 mm² sensor dimension; FIG. 2aa). The antibody purified in Example 1 was immobilized on the interdigitated area of the NC membrane by the chemical method as described in Example 2.

To position electric contacts on the electrode, silver paste was printed on a plastic film (for a copying machine PP-3300, 5×2.5 mm²) in a two-fingered configuration and baked at 100° C. for 3 min. This plastic was mounted on the topside of the membrane electrodes with immobilized antibody by using a double-sided tape. The two compartments were electrically connected by manually applying the silver paste to prepare thick-film electrodes.

EXAMPLE 8

Construction of Electrochemical Membrane Biosensor System I

The electrochemical membrane biosensor system according to the present invention was constructed. The structure is as shown in FIG. 2aa. A glass fiber membrane (5×25 mm) treated with 0.1% (v/v) Tween-20 was used as membrane pad for sample application (10), NC membrane (5×20 mm) as membrane pad for signal generation (20), and cellulose membrane (5×35 mm) as membrane pad for absorption (30). Onto the signal generation membrane pad, electrodes were screen-printed by the process as in Example 7 and antibody was immobilized between the two electrodes by the procedure of Example 2.

Gold-antibody conjugate solution (5 μl) prepared in Example 3 was applied onto the glass membrane at the site of 15 mm from the bottom end and then dried. Each membrane strip was partially superimposed and attached onto a plastic film using a both-sided tape.

EXAMPLES 9 to 11

Construction of Electrochemical Membrane Biosensor System II

Except using the polyaniline-bound conjugates prepared in Examples 4, 5 and 6 instead of that of Example 3, the electrochemical membrane biosensor system according to the present invention were constructed by the same procedure as in Example 8.

COMPARATIVE EXAMPLE 1

Construction of Membrane Strip Immunosensor System for Photometric Assay

As a comparative example, the conventional membrane chromatographic assay system for the naked-eye determination or optical density measurement was constructed. The structure is as shown in FIG. 1, and 0.1% (v/v) Tween-20-treated glass fiber membrane (5×25 mm) was used as sample application pad (10), NC membrane (5×20 mm) as signal generation membrane pad (20) and cellulose membrane (5×35 mm) as absorbent membrane pad (30). The antibody was immobilized on the signal generation membrane pad by following the procedure in Example 2. 5 μl of the gold-antibody conjugate solution prepared in Example 3 was applied onto the glass membrane at the site of 15 mm from the bottom end and dried in the ambient air. Each membrane strip was partially superimposed and attached to a plastic film by a double-sided tape.

EXPERIMENTAL EXAMPLE 1

Assay I by Using Electrochemical Detection System: Experiment on the Effect of Polyaniline To obtain responses of the electrochemical assay system of the present invention to standard concentrations of HSA, the following experiment was carried out (FIG. 1).

10 μg/ml of a HSA standard solution was prepared by diluting it with 10 mM Tris buffer including 0.01% (v/v)

Tween-20, and 150 μl of this solution was transferred into different microwells. The bio-strip sensor systems prepared in Example 8 (without polyaniline), Example 9 (0.01 mg/ml of polyaniline), Example 10 (0.1 mg/ml of polyaniline) and Example 11 (1 mg/ml of polyaniline) were placed within each microwell in an erect position. The aqueous solution was absorbed for about 6 min from the bottom end of the strip and dose response data were collected by using the conductimetric detection. Prior to carrying out the measurement, conductivity meter (Model 150, Orion Corp., Beverly, Mass., USA) was calibrated by using a screen-printed plastic electrode prepared under the same conditions as for the NC membrane electrode. The electrode was automatically calibrated by immersing in a 0.01 M KCl standard solution (specific conductance: 1413 μS/cm, total dissolved solids: 692 ppm as NaCl). After extensive washing, the electrode was immersed again in deionized water and set to zero. Under these conditions, the cell constant distributed between 0.475 to 1 $cm^{-1}$. The meter was then used to measure the conductivities as responses of the bio-strip sensor to variable analyte concentrations.

Figure 4:
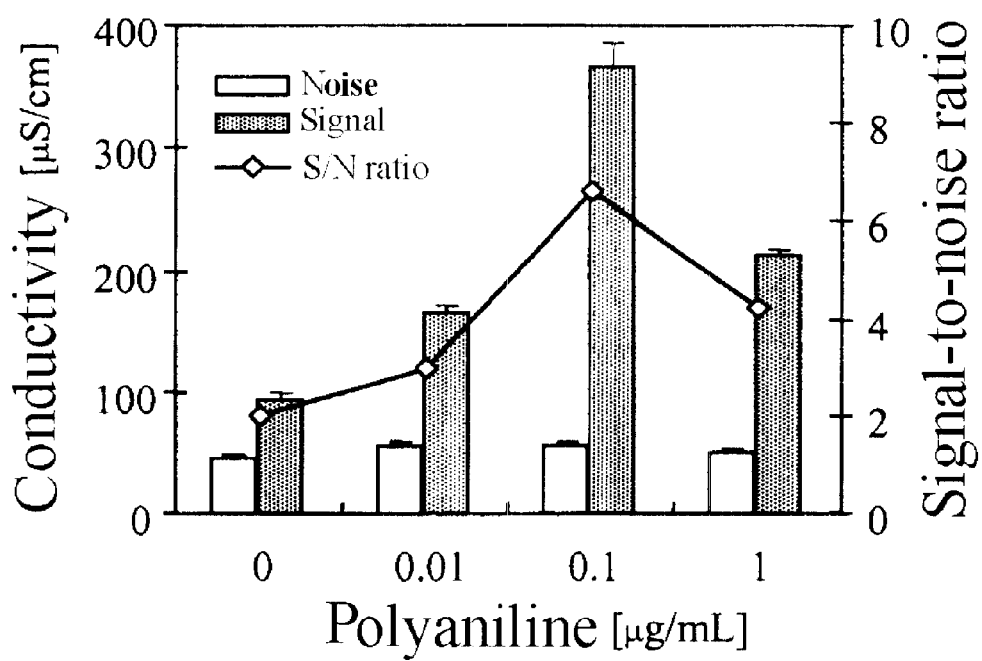
FIG. 4 shows a change in conductivity and signal-to-noise ratio against polyaniline concentration (0 mg/ml, Example 8; 0.01 mg/ml, Example 9; 0.1 mg/ml, Example 10; and 1 mg/ml, Example 11), which is used as conducting polymer in the electrochemical membrane strip biosensor according to the present invention.

As shown in FIG. 4, as the gold-conjugated polyaniline concentration increased, the conductimetric signal elevated in proportion to the concentration, but diminished at 1 mg/ml or higher concentrations. Especially, in the high concentration range, upon adding the polyaniline solution, the color of the gold solution changed from red to purple, indicating aggregation of the particles due to cross-linking by the polyaniline molecules. On the other hand, the background signal, i.e., the noise, was kept constant regardless of the amount of the conducting polymer used. In conclusion, the relative intensity of the signal to noise reached a maximum when 0.1 mg/ml of polyaniline (Example 10) was used.

EXPERIMENTAL EXAMPLE 2

Figure 5:
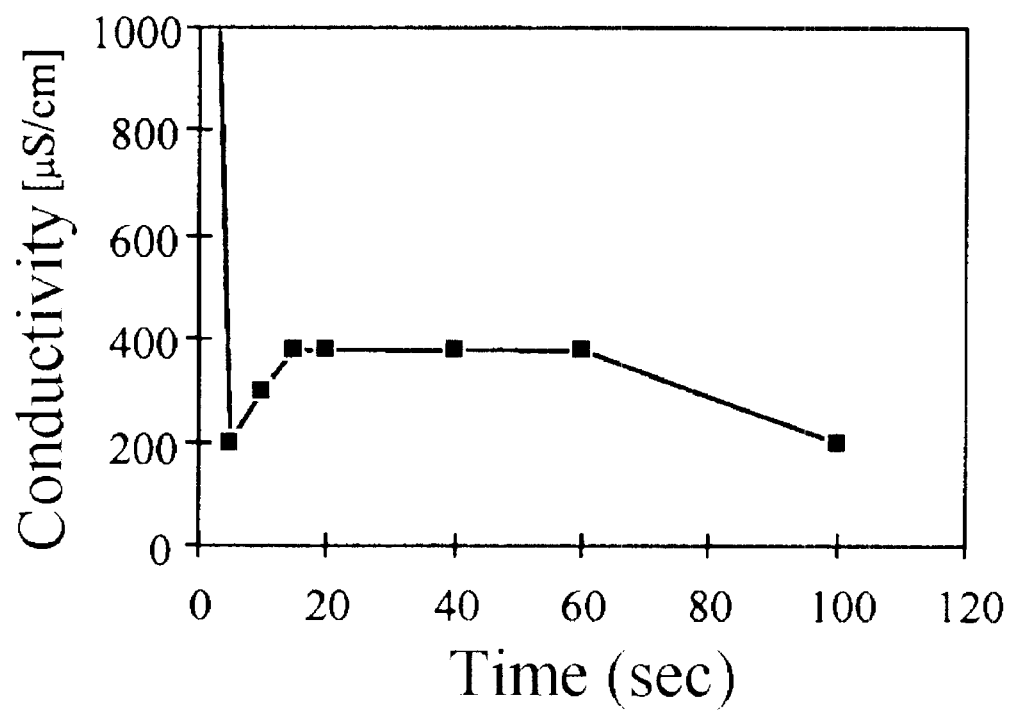
FIG. 5 shows a change of conductivity against time after the binding protein-analyte reaction in assays using the electrochemical membrane strip biosensor of the present invention (Example 10).

Assay II Using Electrochemical Detection System: Experiment on the Effect of Detection Time The electrochemical membrane biosensor prepared in Example 10 was assessed by the same method as in Experimental example 1. To find an optimal electric signal detection time after immune reaction, an initial transient response of the sensor after voltage application was recorded against time. The result is shown in FIG. 5.

Once voltage was applied across the electrodes, electrochemical reactions occurred on the electrode surfaces and initially caused a fluctuation in the electric conduction from a few seconds to about 1 min depending on the density of the conjugate (i.e. gold) bound. However, the signal quickly became steady and the conductivity was measured. The conductivity, thereafter, gradually decreased, which was probably caused by the drying of the membrane strip in the air. Therefore, in actual measurement, it would be preferable to read a steady value between 30 and 60 seconds after voltage application.

EXPERIMENTAL EXAMPLE 3

Assay III Using Electrochemical Detection System: Evaluation of Electrochemical Assay Performances The electrochemical membrane biosensor prepared in Example 10 was evaluated by comparing the performances to HSA standard solutions with those of the photometric membrane immuno-sensor prepared in Comparative Example 1.

HSA standard solutions were prepared by diluting with 10 mM Tris containing 0.01% (v/v) Tween-20 to a series of concentrations, 0.01, 0.1, 1, 2.5, 5, 10 and 50 μg/ml, and 150 μl of each concentration was placed into microwells.

Analytical procedure with the electrochemical membrane biosensor prepared in Example 10 was identical to that in Experimental example 1 except that the response was measured at 60 seconds after voltage application.

In measurement with the photometric membrane immunosensor prepared in Comparative Example 1, color signals as dose responses to HSA standard solutions were determined based on scanning photometry. HSA standard solutions were prepared using 10 mM Tris containing 0.01% (v/v) Tween 20, and 150 μl of each concentration was applied to distinct microwells. The bottom end of the membrane strip immunosensors prepared in Comparative Example 1 were immersed within each microwell in an erect position, and the solutions were absorbed into strips for about 6 min. The color signal appeared at the area of the immobilized antibody was quantified by a scanner (HP ScanJet 6100C, Hewlett-Packard, Palo Alto, Calif., USA). After scanning the colored strip, a membrane image was captured by a scanning board and software (Biomed Instruments, USA) installed within computer. The colored area of the captured image was converted to optical density, which is in proportion to color intensity, by utilizing an image analysis program (Multianalyst version 1.1, Bio-Rad laboratories, Hercules, Calif., USA).

Figure 6A:
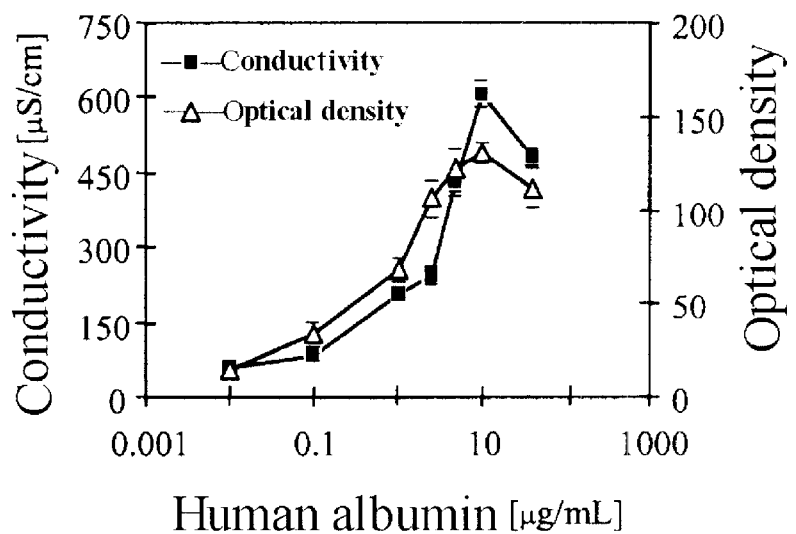
FIG. 6 shows the measured signals (FIG. 6a) and the signal-to-noise ratios calculated from the values (FIG. 6b) against standard concentrations of human serum albumin, respectively, which were determined by using the electrochemical membrane strip biosensor prepared in Example 10 and the conventional photometric membrane strip prepared in Comparative Example 1.

The result is shown in FIG. 6. FIG. 6a exhibits the dose responses based on conductimetry and photometry. Although both of the two different signals, conductivity and optical density, were directly proportional to the analyte dose up to the point where a hook effect (the phenomenon of signal decrease occurred in high concentrations of analyte) became apparent, their response patterns were quite different. In the semi-log plot (Reference: J. H. Petermen, Immunochemistry of Solid-Phase Immunoassay, 1991, page 47–65, CRC Press, London) excluding the hook area, while the photometric signal showed a conventional, sigmoidal curve, the electrochemical signal showed an exponential shape.

Figure 6B:
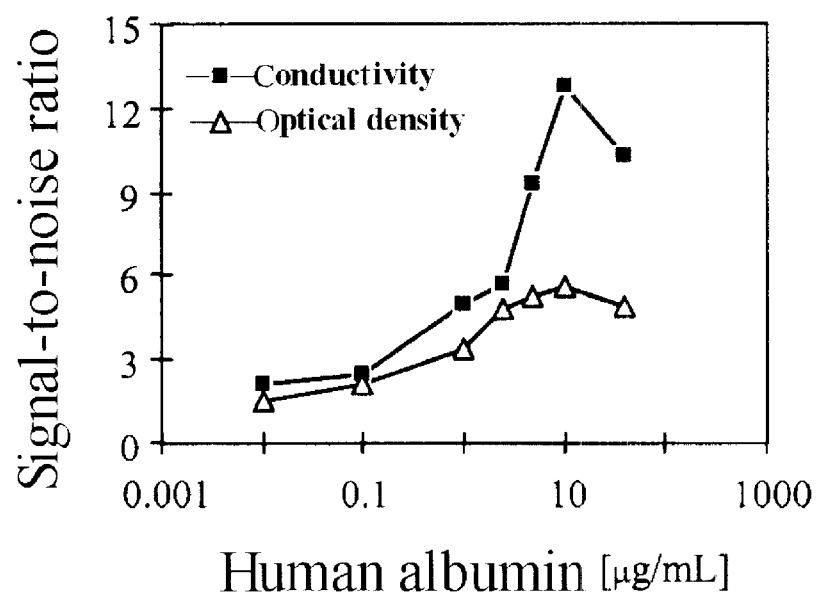

To compare their performances, the dose response signals were converted to signal-to-noise ratios for each analyte concentration (FIG. 6b). The signal-to-noise ratio measured by conductimetry was higher over the whole range of the analyte concentration than those by photometry, further increased up to 2.3 fold under the test conditions used.

As results, it was demonstrated that conductimetric determination exhibits a signal amplification effect as well as noticeable dose responses in an exponential pattern.

What is claimed is:

1. An electrochemical membrane strip biosensor comprising
    (a) a first membrane strip pad for sample application;
    (b) a second membrane strip pad, partially superimposed in length with the first membrane strip pad for signal generation, said second membrane strip pad including (i) a binding protein, specifically binding to an analyte, immobilized at a defined area of the second membrane's surface, and (ii) at least one pair of electrodes screen-printed on said second membrane's surface such that the binding protein-immobilized area is located between the two electrodes;
    (c) a third membrane strip pad, partially superimposed in length with the second membrane strip pad for absorption of an aqueous medium; and (d) a conjugate between (i) a binding protein specifically binding to a different site on the analyte from that recognized by said immobilized binding protein of the second membrane strip, and (ii) a metal colloid having surfaces bound by a conducting polymer,
    wherein said conjugate is either placed at a predetermined site on the first membrane strip pad in a dry state or is contained in a separate container and placed on said first strip membrane pad prior to use of the biosensor.

2. The electrochemical membrane strip biosensor of claim 1, wherein the first membrane strip pad is a glass fiber membrane pad, the second membrane strip pad is a nitrocellulose membrane pad, and the third membrane strip pad is a cellulose membrane pad.

3. The electrochemical membrane strip biosensor of claim 1, wherein the binding protein is an antibody, enzyme or receptor that reacts specifically with the analyte.

4. The electrochemical membrane strip biosensor of claim 1, wherein the metal colloid is a gold colloid, silver colloid or iron colloid.

5. The electrochemical membrane strip biosensor of claim 1, wherein the electrodes are screen-printed on an insulator.

6. The electrochemical membrane strip biosensor of claim 1, wherein the electrodes are screen-printed with platinum paste, gold paste, silver paste or carbon paste.

7. The electrochemical membrane strip biosensor of claim 1, wherein the electrodes are interdigitated electrodes formed on the same surface of the second membrane strip pad.

8. The electrochemical membrane strip biosensor of claim 1, wherein electric contacts to the electrodes are present on a lateral side of the second membrane strip.

9. The electrochemical membrane strip biosensor of claim 1, wherein the electrodes are positioned on opposite sides of the second membrane strip pad to form a sandwich-type electrode.

10. The electrochemical membrane strip biosensor of claim 9, wherein at least two pairs of electrodes are present to determine at least two different analytes simultaneously.

11. The electrochemical membrane strip biosensor of claim 1, wherein the conjugate is prepared by adsorbing the binding protein on surfaces of the metal colloid, subsequently binding the conducting polymer thereon, and then adsorbing a blocking protein on residual surfaces of the metal colloid.

12. The electrochemical membrane strip biosensor of claim 11, wherein the conducting polymer alone or treated with a dopant is polyaniline, polypyrrole, polythiophene or poly(p-phenylene), and the blocking protein is bovine serum albumin, casein or gelatin.

13. The electrochemical membrane strip biosensor according to claim 12, wherein the dopant is (a) an ionic salt with or without redox molecules chemically bound to said conducting polymer, or (b) a polymeric counterion non-covalently interacting with said conducting polymer.

* * * * *